United States Patent [19]

Trani et al.

[11] Patent Number: 5,559,249

[45] Date of Patent: Sep. 24, 1996

[54] 7'-AMINO-NAPHTHAZARIN ANTIBIOTIC DERIVATIVES

[75] Inventors: Aldo Trani; Clelia M. L. Dallanoce, both of Milan; Romeo Ciabatti, Novate Milanese, all of Italy

[73] Assignee: Gruppo Lepetit Spa, Gerenzano, Italy

[21] Appl. No.: 450,194

[22] Filed: May 25, 1995

[62] Division of PCT/EP92/02764, Nov. 30, 1992 published as WO93/12115, Jun. 24, 1993.

[30] Foreign Application Priority Data

Dec. 18, 1991 [EP] European Pat. Off. .............. 91121674
Oct. 22, 1992 [EP] European Pat. Off. .............. 92118035

[51] Int. Cl.$^6$ ................................................. C07D 493/20
[52] U.S. Cl. ................................................................ 549/264
[58] Field of Search ................................................ 549/264

[56] References Cited

U.S. PATENT DOCUMENTS 5,475,010  12/1995  Trani et al. .............................. 514/318

*Primary Examiner*—Amelia Owens
*Attorney, Agent, or Firm*—J. Michael Dixon

[57] ABSTRACT

Compound of general formula V

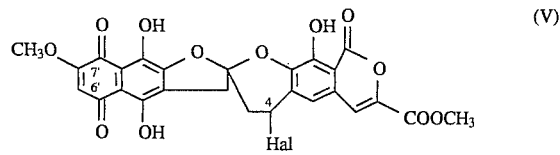

wherein Hal is a chlorine or bromine atom.

The compounds are useful as starting materials in preparing gamma-rubromicin amino derivatives.

4 Claims, No Drawings

7'-AMINO-NAPHTHAZARIN ANTIBIOTIC DERIVATIVES

This application is a divisional of PCT/EP92/02764, Jun. 24, 1993 which was filed on Nov. 30, 1992, now WO 93-12115 designating the United States and which entered the national phase of the U.S. on May 26, 1994, under 35 USC 371 and was assigned application Ser. No. 08/244,353 now U.S. Pat. No. 5,475,010.

The present invention concerns novel naphthazarin antibiotic derivatives having general formula I

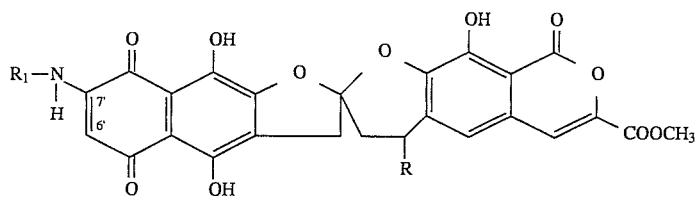

and the pharmaceutically acceptable addition salts thereof, wherein:

R represents hydrogen or hydroxy;

$R^1$ represents hydrogen or an —alk-X group wherein alk represents a ($C_1$–$C_4$) alkylene and X represents hydrogen, hydroxy, cyano, trifluoromethyl, phenyl, mono-, di- or tri-substituted phenyl wherein the substituents are independently selected from ($C_1$–$C_4$) alkyl, ($C_1$–$C_4$) alkoxy, hydroxy, amino, halogen, nitro and sulphonyl, or a —$NR^2R^3$ group wherein $R^2$ and $R^3$ independently represent hydrogen, ($C_1$–$C_4$) alkyl or an amino-protecting group selected from ($C_1$–$C_5$)alkoxycarbonyl, ($C_2$–$C_4$)alkenyloxycarbonyl, cinnamyloxycarbonyl, benzyloxycarbonyl, p-nitrobenzyloxycarbonyl, 3,4-dimethoxy-6-nitrobenzyloxy-carbonyl, 2,4-dichloro-benzyloxycarbonyl, 5-benzylisoxazolylmethoxycarbonyl, 9-anthranylmethoxycarbonyl, These novel naphthazarin antibiotic derivatives are characterized by having an amino or monosubstituted amino group linked to the 7' position of the molecule.

Preferred compounds are those of formula 1 wherein
R is hydrogen or hydroxy;
$R^1$ represents hydrogen or an -alk-X group wherein alk is a methylenic, ethylenic or propylenic moiety;
X is hydrogen, hydroxy, cyano, trifluoromethyl, phenyl or a —$NR^2R^3$ group wherein $R^2$ and $R^3$ independently represent hydrogen, methyl or butyloxycarbonyl.

Most preferred compounds are those wherein R is hydroxy, alk is methylen and X is hydrogen.

In the present description, the terms used above in defining the meanings of R and $R^1$ are intended to have the meanings commonly assigned to them in the art.

The following list exemplifies in particular some of them:

($C_1$–$C_4$) alkylene represents a bifunctional linear or branched hydrocarbon moiety containing 1, 2, 3 or 4 carbon atoms such as:
—$CH_2$—,
—$CH_2$—$CH_2$—,
—$CH(CH_3)$—
—$CH_2$—$CH_2$—$CH_2$—,
—$CH(CH_3)$—$CH_2$—,
—$CH_2$—$CH_2$—$CH_2$—$CH_2$—,
—$CH(CH_3)$—$CH_2$—$CH_2$—,
—$C(CH_3)_2$—$CH_2$—;

($C_1$–$C_4$) alkyl represents a linear or branched hydrocarbon moiety containing 1, 2, 3 or 4 carbon atoms such as:
—$CH_3$,
—$CH_2$—$CH_3$,
—$CH_2$—$CH_2$—$CH_3$,
—$CH$—$(CH_3)_2$,
—$CH_2$—$CH_2$—$CH_2$—$CH_3$,
—$CH(CH_3)$—$CH_2$—$CH_3$,
—$CH_2$—$CH(CH_3)$—$CH_3$,
—$C$—$(CH_3)_3$;

($C_1$–$C_4$) alkoxy represents a linear or branched ether moiety containing 1, 2, 3 or 4 carbon atoms such as:
—O—$CH_3$,
—O—$CH_2$—$CH_3$,
—O—$CH_2$—$CH_2$—$CH_3$,
—O—$CH$—$(CH_3)_2$,
—O—$CH_2$—$CH_2$—$CH_2$—$CH_3$,
—O—$CH(CH_3)$—$CH_2$—$CH_3$,
—O—$CH_2$—$CH(CH_3)$—$CH_3$,
—O—$C$—$(CH_3)_3$;

($C_1$–$C_5$) alkoxycarbonyl and ($C_2$–$C_4$) alkenyloxycarbonyl represent a linear or branched hydrocarbon moiety from 1 to 5 and from 2 to 4 carbon atoms, respectevely, containing a carboxylic function, such as:
—CO—O—$CH_3$,
—CO—O—$CH_2$—$CH_3$,
—CO—O—CH=$CH_2$,
—CO—O—$CH_2$—$CH_2$—$CH_3$,
—CO—O—CH—$(CH_3)_2$,
—CO—O—CH=CH—$CH_3$,
—CO—O—$CH_2$—$CH_2$—$CH_2$—$CH_3$,
—CO—O—$CH(CH_3)$—$CH_2$—$CH_3$,
—CO—O—$CH_2$—$CH(CH_3)$—$CH_3$,
—CO—O—C—$(CH_3)_3$,
—CO—O—$CH_2$—$CH_2$—$CH_2$—$CH_2$—$CH_3$,
—CO—O—$CH_2$—$CH_2$—$CH_2(CH_3)_2$,
—CO—O—C—$(CH_3)_2$—$CH_2$—$CH_3$;

halogen represents a chlorine, bromine or iodine atom.

Examples of compounds which form part of the present invention are:
7'-amino purpuromycin
7'-amino γ-rubromycin
7'-(2-dimethylamino)ethylamino purpuromycin
7'-(2-dimethylamino)ethylamino γ-rubromycin
7'-(phenylmethylen)amino purpuromycin
7'-(phenylmethylen)amino γ-rubromycin
7'-(2-(4-hydroxyphenyl)ethylen)amino purpuromycin
7'-ethylamino purpuromycin
7'-ethylamino γ-rubromycin
7'-propylamino purpuromycin
7'-butylamino purpuromycin
7'-methylamino purpuromycin
7'-methylamino γ-rubromycin
7'-(cyanomethylen)amino purpuromycin
7'-(cyanoethylen)amino purpuromycin
7'-(2-(N-butyloxycarbonyl-amino)ethylamino)purpuromycin
7'-(2-hydroxy)ethylamino purpuromycin
7'-(2-hydroxy)ethylamino γ-rubromycin 7'-(2,2,2-trifluoro)ethylamino purpuromycin and the pharmaceutically acceptable salts thereof.

A further object of this invention is to provide a process for preparing these 7'-amino or 7'-substituted amino naphthazarines of formula 1 by starting from the corresponding 7'-methoxy compound.

Purpuromycin and γ-Rubromycin, which belong to the class of quinonic naphthazarines, are known antimicrobial agents against Gram-positive and Gram-negative bacteria.

Purpuromycin is an antibiotic produced by *Actinoplanes ianthinogenes nov. sp.* A/1668 which was deposited at the American Type Culture Collection (ATCC) of Rockville, Md. 20852 USA on Jan. 29, 1973, where it received the accession number ATCC 21884. This strain was accepted under the conditions of the Budapest Treaty as of Jan. 31, 1981. *Actinoplanes ianthinogenes nov. sp.* A/1668 was described in U.S. Pat. No. 3,914,257.

Purpuromycin, which is useful in the treatment of infectious vaginitis and for the preparation of topical dosage forms for said treatment (see European Patent Application Publication No. 389924, corresponding to U.S. Ser. No. 07/497,378), corresponds to the compound of the general formula I above wherein R is hydroxy and in position 7' there is a methoxy group instead of the —NH—$R^1$ group. Its preparation is described in U.S. Pat. No. 3,914,257 wherein its antimicrobial activity is also reported.

According to U.S. Pat. No. 3,914,257 purpuromycin is active in vitro against both Gram-positive and Gram-negative bacteria and fungi, including filamentous fungi (e.g., *Trichophyton mentagrophytes*) and yeasts (e.g., *Candida albicans*).

Pharmaceutically acceptable water soluble addition salts of purpuromycin are described in U.S. Pat. No. 5,118,705.

γ-Rubromycin is an antibiotic which was isolated from *Streptomyces Collinus* and *S. antibioticus* (Brockmann, H. et al. Chem. Ber. 1969, 102, 126; 1970, 103, 1709; Naegeli, H. U. et al, Helv. Chim. Acta, 1980, 63, 1400) and corresponds to the compound of formula I above wherein R is hydrogen and in position 7' there is a methoxy group instead of the —NH—$R^1$ group.

The above antibiotics can be used as suitable starting materials for the process herein described.

The replacement of the 7' methoxy group of purpuromycin or γ-rubromycin with an aminic group provides new compounds with an improved antimicrobial spectrum, due to a reduced binding to serum proteins, and better physico-chemical characteristics.

The direct introduction of substituents into naphthazarin derivatives by standard reactions appears however to be particularly difficult. For instance it is described that addition of amines to simple naphthazarin derivatives is slow and requires a large excess of reactant (Bruce D. B. and Thomson R. H., J. Chem. Soc., 1955, 1089).

Furthermore, in the specific case of purpuromycin, the selective removal of the 7' methoxy group cannot be performed in the presence of strong acid or basic reagents since demolition of the molecule can easily occur with formation of isopurpuromycin (Bardone M. R., et al. Structure determination of purpuromycin, a new antibiotic, Tetrahedron 30, pp. 2747–2754; 1974), due to the opening of the spiroketal group.

Therefore a further aim of the present invention is to provide a process for preparing a compound of formula I, wherein R and $R^1$ are as above described, which comprises:

a) On a compound of general formula II,

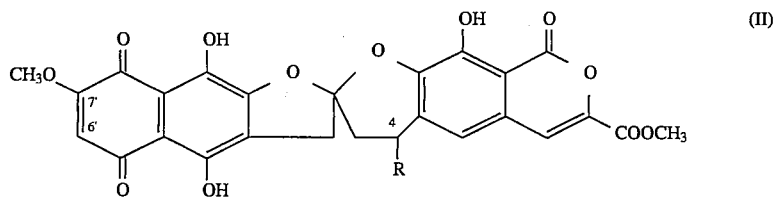

wherein R represents hydrogen, hydroxy or halogen, when R represents an hydroxy group, protecting this hydroxy group, which is linked to the spiroketal moiety, by reacting it with a compound able to form a substituted ($C_1$–$C_3$)alkyl ether or an heterocyclic ether;

b) protecting the remaining hydroxy groups linked to the aromatic moiety of said compound of general formula II, by reacting it with a compound able to form a ($C_1$–$C_3$) alkyl or aryl ester or a carbonate with such hydroxy group;

c) submitting the obtained compound to an electrophylic substitution in position 6' by reacting it with a reactant able to insert in position 6' a moiety selected from ($C_1$–$C_5$) alkylmercapto, phenylmercapto, mono- or di- substituted phenyl mercapto wherein the substituents are selected from ($C_1$–$C_5$) alkyl and halogen, ($C_1$–$C_5$) alkylsulfinyl, phenylsulfinyl, mono- or di- substituted phenylsulfinyl wherein the substituents are selected from ($C_1$–$C_5$) alkyl and halogen, ($C_1$–$C_5$) alkylsulfonyl, phenylsulfonyl, mono- or di- substituted phenylsulfonyl wherein the substituents are selected from ($C_1$–$C_5$) alkyl and halogen, ($C_1$–$C_5$) alkylsulfonium hydrohalide salt, Cl and Br;

d) when R in the obtained compound represents a protected hydroxy function, selectively removing the protective group, by means of an hydrolytic cleavage;

e) reacting the obtained compound in the presence of an organic aprotic solvent with a monosubstituted amine of general formula III

wherein $R^1$ represents hydrogen or an -alk-X group wherein alk represents a ($C_1$–$C_4$) alkylene and X represents hydrogen, hydroxy, cyano, trifluoromethyl, phenyl, mono-, di- or tri-substituded phenyl wherein the substituents are independently selected from ($C_1$–$C_4$) alkyl, ($C_1$–$C_4$) alkoxy, hydroxy, amino, halogen, nitro and sulphonyl, or a —$NR^2R^3$ group wherein $R^2$ and $R^3$ independently represent hydrogen, ($C_1$–$C_4$) alkyl or an amino-protecting group selected from ($C_1$–$C_5$)alkoxycarbonyl, ($C_2$–$C_4$)alkenyloxycarbonyl, cinnamyloxycarbonyl, benzyloxycarbonyl, p-nitrobenzyloxycarbonyl, 3,4-dimethoxy-6-nitrobenzyloxy-carbonyl, 2,4-dichloro-benzyloxycarbonyl, 5-benzylisoxazolylmethoxycarbonyl, 9-anthranylmethoxycarbonyl, diphenylmethoxycarbonyl, isonicotinyloxycarbonyl and S-benzyloxycarbonyl.

f) Submitting the obtained amino-derivative to a selective hydrogenation in order to replace the substituent group in position 6' and, when R represents halogen, the halogen in position 4 with an hydrogen atom, in the presence of an hydrogenation catalyst and of a water miscible aprotic organic solvent.

The protection of the hydroxy groups of the naphthazarin starting material is usually carried out in two steps since not all the hydroxy groups of the molecule need the same kind of protecting groups.

Generally the hydroxy group which is linked to the spiroketal moiety (if present) is protected first and then the hydroxy groups linked to the aromatic rings of the molecule (i.e. the phenol hydroxy goups) are protected.

The protecting groups which can conveniently be employed for protecting the hydroxy group linked to the spiroketal moiety are substituted ($C_1$–$C_3$) alkyl ethers or heterocyclic ethers such as for instance tetrahydro-pyranyl ethers and tetrahydrofuranyl ethers.

However, any typical protecting group of the hydroxy function which selectively protects the spiroketal hydroxy group, which is resistant to the conditions applied during the other protecting steps of the process and which can readily be removed, can be here utilized.

Suitable protecting groups of the hydroxy function are, for instance, described in: T. W. Greene, "Protective Groups in Organic Synthesis", J. Wiley, N.Y. 1981.

Example of suitable protecting groups are those which form a substituted ($C_1$–$C_3$)alkyl ether or thioether function with the hydroxy group of the compound of formula II, such as methylthiomethyl, 2-methoxyethoxymethyl, 2,2,2-trichloroethoxymethyl, bis(2-chloroethoxy)-methyl, 1-ethoxyethyl, 1-isopropoxyethyl, or an heterocyclic ether such as tetrahydropyranyl, 3-bromo-tetrahydro-pyranyl, tetrahydrothiopyranyl, 4-methoxy-tetrahydro-pyranyl, 4-methoxy-tetrahydrothiopyranyl, tetrahydrofuranyl or tetrahydrothiofuranyl.

The preparation of naphthazarin antibiotic starting material protected on the hydroxy groups of the spiroketal moiety is conducted according to the common methods known in the art; for instance in the case that a tetrahydropyranyl ether is used as protecting group, the antibiotic starting material is reacted with the corresponding vinyl ether (i.e. 3,4-dihydropyran) in presence of a mild acid (for instance camphosulfonic acid) in an inert organic solvent such as tetrahydrofuran.

After having recovered, washed and dried the protected antibiotic starting material it is necessary to protect the remaining free hydroxy groups.

In this step any protecting group of the phenolic hydroxy function which is easily removable under the reaction conditions can be favorably used. All the protecting groups for phenols described in the already mentioned book "Protective Groups in Organic Synthesis" can be employed.

Preferred protecting groups are those which are readily cleaved by saponification, such as for instance alkyl or aryl esters which are generally obtained by reacting the phenolic hydroxy groups with acyl chloride or anhydride in the presence of a base (examples of protecting groups are acetate pivaloate and benzoate). Also carbonates such as methyl carbonate, aryl 2,2,2-trichloroethyl carbonate and benzyl carbonate can conveniently be used.

It has been found that the complete protection of the hydroxy groups favours the electrophylic substitution at position 6' of the molecule.

The electrophylic substituents introduced in position 6' can be any group with electro-withdrawing properties. Suitable substituents are ($C_1$–$C_5$) alkylmercapto, phenylmercapto, mono- or di- substituted phenyl mercapto wherein the substituents are selected from ($C_1$–$C_5$) alkyl and halogen, ($C_1$–$C_5$) alkylsulfinyl, phenylsulfinyl, mono- or di- substituted phenylsulfinyl wherein the substituents are selected from ($C_1$–$C_5$) alkyl and halogen, ($C_1$–$C_5$) alkylsulfonyl, phenylsulfonyl, mono- or di- substituted phenylsulfonyl wherein the substituents are selected from ($C_1$–$C_5$) alkyl and halogen, ($C_1$–$C_5$) alkylsulfonium hydrohalide salt, Chloro and Bromo, which are removable under the hydrogenation conditions of step f. Among these —Cl and —Br are preferred, and most preferred is —Br.

The halogenation reaction (bromination or chlorination) may be carried out according to any method known in the art.

For instance the protected antibiotic substrate can be brominated or chlorinated by treatment with bromine or chlorine in presence of a catalyst, most often iron which forms the active ferric bromide or ferric chloride reactant, or by direct action of $Br_2$ and $Cl_2$ in water or in an inert organic solvent at room temperature.

Other reactants which can be used are HOCl, HOBr and N-chloro and N-bromo imides (for instance N-bromo succinimide). In these instances the reaction is catalyzed by adding an organic acid.

Preferred reactants for halogenating the naphthazarin antibiotic substrates of the invention are $Cl_2$ in acetic acid and chloroform ($CHCl_3$) or pyridine bromide perbromide ($PyBr_2$ HBr) in dichloroethane ($CH_2Cl_2$).

Generally the chlorinating compounds are more reactive than the brominating ones; nevertheless the bromination reaction is oftentimes preferred because of the higher selectivity of the brominating reactants.

The removal of the protection of the hydroxy group linked to the spiroketal moiety, if present, is conducted as known in the art with respect to the protecting agent that is used. For instance when tetrahydropyranyl is used as the protecting group it is cleaved by action of a HCl (1N) solution in acetone, or p-toluensolfonic acid in methanol.

It is evident to a man skilled in the art that this deprotection step can be performed either before or after the amination reaction (step e).

After the electrophilic substituent has been introduced at position 6' as reported above, the desired amination is conveniently carried out by reacting the compound, in presence of an inert organic solvent, with an amine of the above specified general formula III.

Inert organic solvents useful for the above described reaction steps, as here intended, are those organic solvents which are inert under the conditions of the specific reaction step, do not unfavorably interfere with the reaction course and are capable of at least partially solubilizing the antibiotic material.

Examples of said inert organic solvents are organic amides, alkyl ethers of glycols and polyols, phosphoramides, sulfoxides and aromatic compounds. Preferred examples of inert organic solvents are: dimethylformamide, dimethoxyethane, hexamethylphosphoramide, dimethylsulfoxide, tetrahydrofuran (THF) and mixtures thereof, tetrahydrofuran beeing the preferred one.

The reaction temperature may vary considerably depending on the specific starting materials and reaction conditions. In general, it is preferred to conduct the reaction at temperatures between 0° C. and 40° C.

Also the reaction times vary considerably depending on the other reaction parameters. In general the amination reaction vary from 30 minutes for the most reactive amines, up to 80 hours for the less reactive ones. The reaction path can be monitored by TLC or preferably by HPLC according to the methods known in the art. Based on the evaluation of these assays, a man skilled in the art will be able to stop the amination reaction at a due time and start working up the reaction mass, according to known per se techniques which include for instance extraction with solvents, precipitation by addition of nonsolvents, etc.

It is normally preferred that the molar ratio amine÷substrate be generally greater than the stoichometric one (1÷1). In this case the cleavage of the acyl protection of the phenolic hydroxy groups can be obtained. The molar ratio can vary from 1.2÷1, for the most basic amines, up to 10÷1.

When in the final mixture is still present a substantial amount of unreacted compound, more particularly when ammonium hydroxide is employed, a further treatment can be performed according to the reaction conditions outlined above to complete the conversion to the desired 7' amino compound.

After the ammination step (e) has been performed, a compound of general formula IV is obtained:

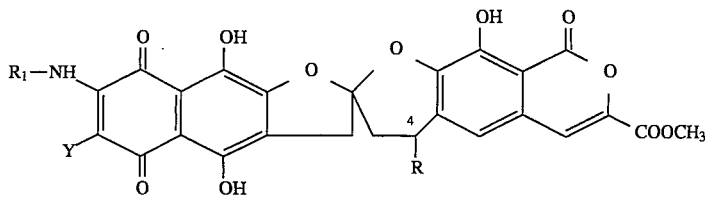

(IV)

either unsalified or as a base addition salt, wherein:

R and $R^1$ are as defined in formula 1 and Y represents a group selected from ($C_1$–$C_5$) alkylmercapto, phenylmercapto, mono- or di- substituted phenyl mercapto wherein the substituents are selected from ($C_1$–$C_5$) alkyl and halogen, ($C_1$–$C_5$) alkylsulfinyl, phenylsulfinyl, mono- or di- substituted phenylsulfinyl wherein the substituents are selected from ($C_1$–$C_5$) alkyl and halogen, ($C_1$–$C_5$) alkylsulfonyl, phenylsulfonyl, mono- or di- substituted phenylsulfonyl wherein the substituents are selected from ($C_1$–$C_5$) alkyl and halogen, ($C_1$–$C_5$) alkylsulfonium hydrohalide salt, Cl and Br.

After the reaction mixture has been separated and the compound of general formula IV has been recovered, in order to transform it in a compound of formula 1, it is necessary to replace the activating group in position 6', and, if present, the halogen atom in position 4 with an hydrogen atom. Usually this is done under hydrogenation conditions in presence of a suitable hydrogenation catalyst.

Suitable hydrogenation catalysts for the process of the present invention are Palladium, Platinum, or Rhodium as such or preferably supported on a conventional carrier. The preferred catalyst is Palladium on carbon. This catalyst is preferably used at a concentration between 3% and 10% (w/w) (i.e. from 3% to 10% Palladium on carbon), 5% Palladium on carbon being the most preferred.

Palladium on carbon is preferably employed when the reaction is conducted at room pressure and temperature, while 3% Palladium on Barium sulfate is preferably employed when the reaction is conducted at room temperature and at a pressure of 5 atm (about 490 KPa).

The proportion between the substrate to be hydrogenated and the catalyst may vary considerably. In general, these substances are contacted, on a weight to weight basis, in a proportion from 1:10 to 1:0.8, (catalyst to substrate) depending also on the specific characteristics of the selected catalyst and reaction conditions. Generally a ratio between 1 to 4.5 and 1 to 1 (catalyst to substrate, w/w) is preferred.

The reaction solvent is a water miscible aprotic organic solvent such as an ether (e.g. tetrahydrofuran -THF) or a dialkylacylamide (e.g. dimethylformammide -DMF).

The hydrogenation is preferably performed in the presence of a weakly basic compound in order to promote the removal of the substituent in 6 and, if present the one in 4, while preventing degradative side-reactions. Preferred weakly basic compounds are salts such as sodium, potassium, silver or ammonium ($C_1$–$C_3$)acylates, ammonium hydroxide or mono-, di- or tri- ($C_1$–$C_3$) alkylamines; the salts can be added as such or solubilized in a minimum amount of water.

It is further preferred, particularly when the above mentioned salts are employed, to add a miscible polar organic solvent, such as ($C_1$–$C_4$)alcohols or glycols, to the reaction mixture, to improve the solubilization. The preferred reaction mixtures are THF with methanol and sodium acetate, THF with triethylamine or THF with silver acetate.

The reaction pressure is generally an important parameter in hydrogenation reactions. In general it is related to the type and concentration of the hydrogenation substrate, catalyst and reaction temperature. In the present case it may be between ambient pressure and 5 atm (about 490 KPa). High yields are already obtained at ambient pressure or with a slight hydrogen overpressure (from about 98 to about 147 KPa).

As for the reaction temperature, good results are conveniently obtained by operating at room temperature. Depending on the specific reaction conditions, i.e. type and concentration of the catalyst and solvent, it may be possible or convenient to use higher or lower temperatures.

As it is appreciated by those skilled in the art, the reaction time considerably varies depending on the substrate and the specific reaction conditions. The hydrogenation reaction is generally completed in 30 minutes to 5 hours, but for the less reactive compounds can rise up to 70 hours. However, the reaction course may be monitored by TLC or HPLC techniques as known in the art; for instance, samples may be drawn at intervals and assayed in order to determine when the reaction is complete.

The reaction may then be stopped in order to prevent the negative consequences of a prolonged contact between the final product and the reaction mass. A complementary or alternative procedure for evaluating the reaction time and the end of the hydrogenation process is based on the measure of the absorption of hydrogen by the reaction mass.

Once the reaction is completed, the reaction product is isolated according to known per se techniques. Typically, the catalyst is separated by filtration. The recovered catalyst is washed thoroughly and the pooled filtrates are combined. These liquids contain the reaction product which is then recovered and purified according to known methods such as extraction with solvents, precipitation by addition of nonsolvents, column chromatography and the like.

The following Scheme 1 outlines just a specific exemplification of the process steps described above and has to be considered in no way as limitative of the scope of the present invention. According to what said above, the sequence of the single steps can be changed, without nevertheless changing the final result.

In the specific scheme purpuromycin is used as the starting material and therefore 7'-amino-purpuromycin derivatives can be obtained; the protective group of the hydroxy linked to the spiroketal moiety is tetrahydropyranyl ether whilst the one of the phenolic hydroxy is an acetilic group and the activating group in position 6' is bromine.

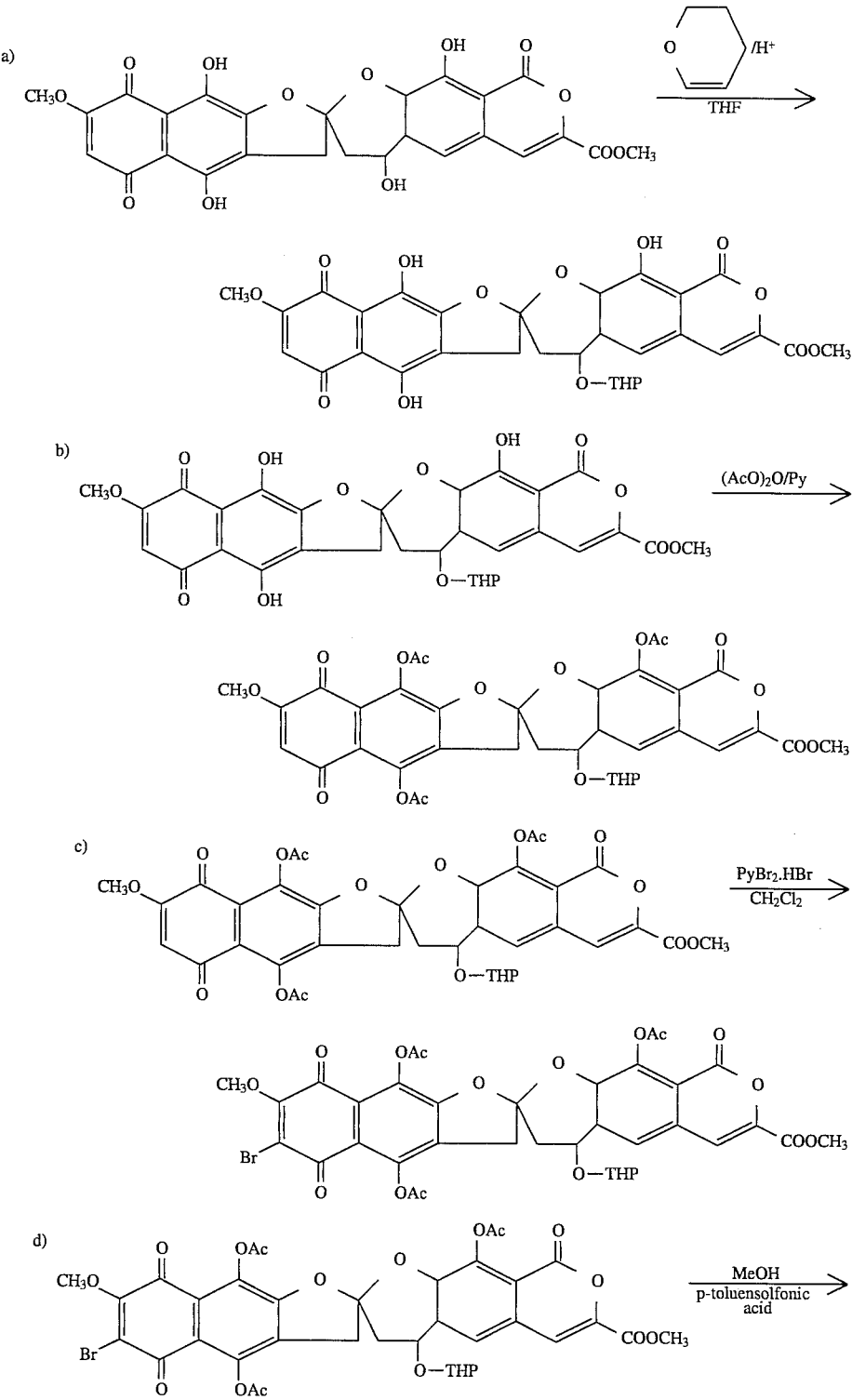

Scheme 1

-continued
Scheme 1

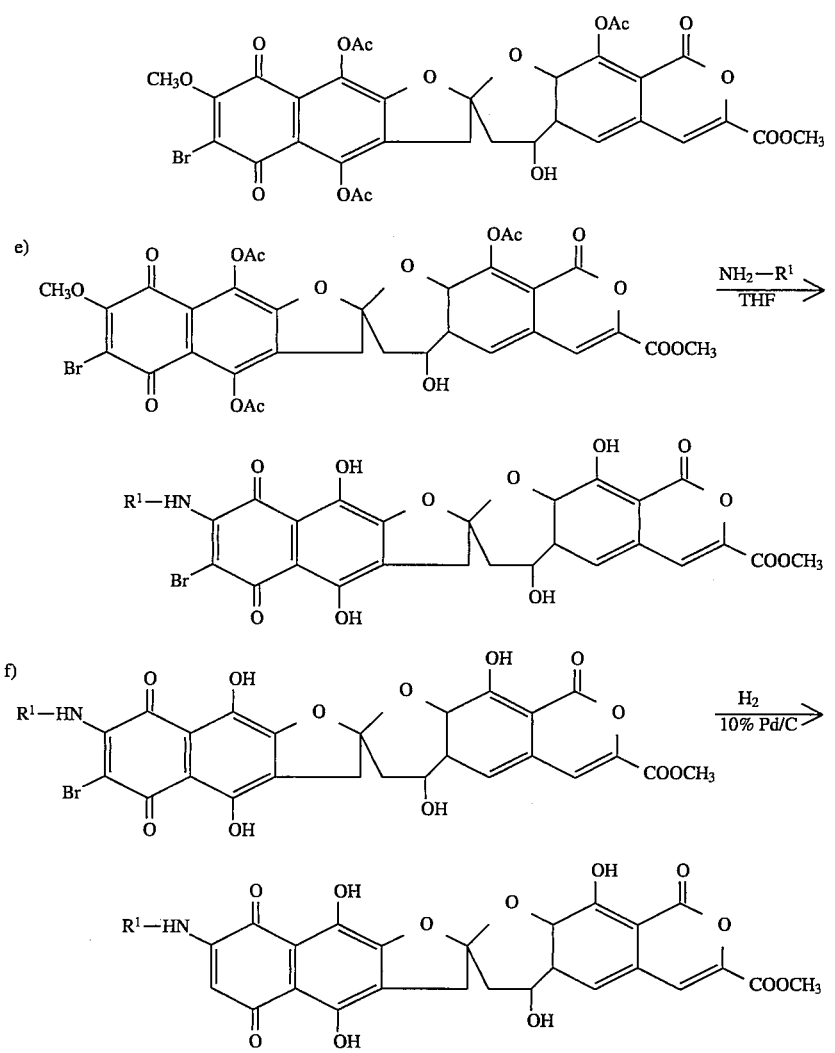

As mentioned above, the 7'-amino or 7'-(substituted-amino) γ-rubromycin derivatives can be obtained by using as starting material a 4-halo-purpuromycin, instead of γ-rubromycin.

4-halo-purpuromycin is produced by a halogenation of purpuromycin in position 4 the halogen group. This halogen group is then easily removable by hydrogenation under the reaction condition of step f, to give the desired 7'-amino-γ-rubromycin derivative.

Suitable reactants for this halogenating step are reported on "Compendium of organic sinthetic methods" (Harrison & Harrison, Vol. 2, pp. 137–139, Vol. 3, pp. 219–221, Wiley-Interscience Publ.). Preferred compounds are thionyl chloride, triphenyl phosphine ($Ph_3P$) or polymer supported $Ph_3P$ in $CCl_4$, $Ph_3P.Cl_2$, $PCl_3$ and $ZnCl_2$ in dimethylformammide, $AsCl_3$, $PBr_3$ and $(CH_3)_2S.Br_2$.

Most preferred reactant is $SOCl_2$, which is preferably used in the presence of pyridine.

As result, the compound of general formula V is obtained:

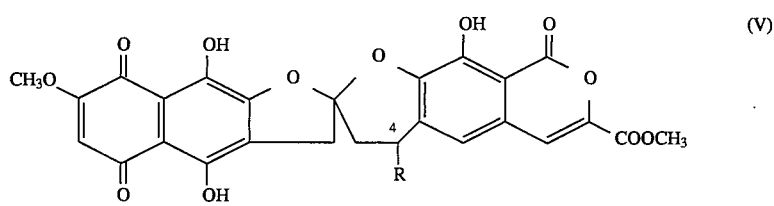

(V)

wherein Hal represents an halogen atom, preferably chlorine or bromine.

This compound can then be employed as the starting material in the the above outlined process steps (a) to (f).

Alternatively, the substitution in position 4 of purpuromycin can be performed after the amination step, step (e) of the process, thus obtaining a compound of general formula IV, wherein $R^1$ and Y have the meanings reported above and R is a halogen group. With the hydrogenation step (f) both the substituents in position 4 and 6' will then be removed, obtaining the desired γ-rubromycin amino derivative.

A further alternative for obtaining γ-rubromycin derivatives is to hydrogenate the hydroxy group in position 4 of a purpuromycin derivative in an independent step, according to the well known per se techniques for hydrogenating a benzylic hydroxy group. For instance, any of the purpuromycin derivatives obtained according to the above outlined process steps a to f, can be reacted in order to insert a tosilate, mesilate or xantate group in the position 4; these derivatives can be subsequently hydrogenated with tri-butyltin hydride and sodium iodide in 1,2-dimethoxyethane (Chemical Letters 1983, p. 795, Chem. Soc. of Jap. ), Raney-Ni in dioxane-($C_1$–$C_4$)alcohol (Am. Chem. Soc., 1955, 77, p. 1820), or $But_3SnH$ and $Et_3B$ in hexane (Tetrahedron Lett., 1988, 29, p. 6125), respectevely.

Preferably the hydrogenation of the 4-hydroxy is performed in a single step, by reacting the obtained purpuromycin derivatives with $NaBH_3CN$ and $ZnI_2$ in dichloroethane (J. Org. Chem. 1986, 51, pp. 3038–3043), $LiAl_4$ and $(Ciclopentadienyl)_2TiCl_2$ in THF (Chem. Lett. 1980, pp. 103–106, Chem. Soc. of Jap.) or $P_2I_4$ in benzene.

The halogenation reaction introduces in position 4 a new chiral center and gives an enantiomeric mixture of 4-halo purpuromycin (R+S). These two enantiomers can be easily separated by well known techniques, for instance using chromatographic techniques. Anyway, for the purpose of this process the separation of the two isomers is not necessary since the last hydrogenation step eliminates this chiral center and can conveniently be carried out without any problem on the enantiomeric mixture.

Pharmaceutically acceptable salts of the compound of general formula I can be formed with both acid or basic reactants.

Basic salts are formed by complete salification of at least one of the three phenolic hydroxy groups by means of amines which impart the desired solubility without modifying the molecular structure of the antibiotic or negatively affecting its stability.

Suitable compounds which may form pharmaceutically acceptable salts with compounds of general formula I are branched or linear mono-, di- or tri-alkylamine wherein the alkyl chain has 2 to 5 carbon and contains at least one hydrophilic substituent selected from OH, SH and $NH_2$ and whose pK value is comprised between 8 and 9.5 and basic natural and synthetic amino acids (e.g. amino acids having an additional amino group), in either L, D or racemic form, having a $pK_3$ value between 10 and 11.

Acid salts can only be formed when the substituent X of the general formula I represents an aminic group of formula —$NR^2R^3$, wherein $R^2$ and $R^3$ have the meanings set forth above.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, palmoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

The antibiotic compounds of the invention are active against Gram positive and Gram negative microorganisms and fungi.

The following table (table 2) reports the antimicrobial activity of representative compounds of the invention.

The minimal inhibitory concentration (MIC) for the microorganisms were determined by broth microdilution methodology. Inocula were approximately $10^4$ colony-forming units per ml (cfu/ml) for bacteria and *Candida albicans* and 1% (v/v) of a suspension of mycelia and conidia for *Trichophyton mentagrophytes*. Incubation was at 37° C. except for *T. mentagrophytes* (30° C.). *Neisseria gonorrhoeae* and *Haemophilus influenzae* were incubated in 5% carbon dioxide in air; *Clostridium perfringens*, *Propionibacterium acnes* and *Bacteroides fragilis* in nitrogen-carbon dioxide-hydrogen (80:10:10); other organisms in air. Incubation times were 48 hours for *N. gonorrhoeae, H. influenzae, C, perfringens, P. acnes* and *B. fragilis*; 72 hours for *T. mentagrophytes*; 20–24 hours for other organisms. The growth media were: Iso-Sensitest broth (Oxoid) for staphylococci, *Enterococcus faecalis, Escherichia coli, Proteus vulgaris* and *Pseudomonas aeruginosa*; Todd Hewitt broth (Difco) for streptococci; GC Base broth (Difco)+1% (v/v) IsoVitaleX (BBL) for *N. gonorrhoeae*; Brain Heart infusion broth (Difco)+1% (v/v) Supplement C (Difco) for *H. influenzae*; Wilkins-Chalgren broth (Difco) for *C. perfringens, P. acnes* and *B. fragilis*; phosphate-buffered Yeast Nitrogen Base broth (Difco) supplemented with glucose (1% w/v) and L-asparagine (0.15% w/v) for *C. albicans*; YM broth (Difco) for *T. mentagrophytes*.

TABLE 2

| Strain | Internal code | MIC of the compounds of examples (μg/ml) | | | | | |
|---|---|---|---|---|---|---|---|
| | | 6 | 8 | 10 | 12 | 14 | 16 |
| *Staphilococcus aureus* Tour | 165 | 0.13 | 0.5 | 0.06 | 0.03 | 0.016 | 0.13 |
| *Staphilococcus aureus* Tour ($10^6$ cfu/ml) | 165 | 0.13 | 1 | 0.06 | 0.03 | 0.06 | 0.13 |
| *Staph. aureus* tour + 30% bovine serum | 165 | 0.25 | 32 | 1 | 2 | 0.25 | 2 |
| *Staphilococcus epidermidis* ATCC 12228 | 147 | 0.13 | 0.13 | 0.06 | 0.016 | 0.008 | 0.13 |
| *Staphilococcus haemolyticus* (clin. isolate) | 602 | 0.5 | 0.13 | 0.06 | 0.06 | 0.016 | 0.13 |
| *Streptococcus pyogenes* C 203 | 49 | 0.13 | 1 | 0.06 | 0.13 | 0.03 | 0.13 |
| *Streptococcus pneumonieae* UC 41 | 44 | 0.06 | 0.06 | 0.06 | 0.03 | 0.016 | 0.03 |
| *Enterococcus faecalis* ATCC 7080 | 149 | 0.13 | 4 | 0.06 | 0.06 | 0.03 | 0.13 |
| *Clostridium perfringens* ISS 30543 | 290 | n.t. | n.t. | n.t. | n.t. | n.t. | 0.13 |
| *Bacteroides fragilis* ATCC 9689 | 1010 | 0.5 | 0.5 | 0.06 | 0.03 | 0.03 | 0.5 |
| *Propionibacterium acnes* ATCC 6919 | 1014 | 0.06 | n.t. | 0.06 | n.t. | 0.008 | 0.016 |
| *Neisseria gonorrhoeae* ISM 68/126 | 997 | 0.13 | 0.25 | 0.06 | 0.06 | 0.06 | 0.06 |
| *Haemophilus influenzae* type b ATCC 19418 | 970 | 0.13 | 2 | 0.06 | 0.13 | 0.13 | 0.13 |

TABLE 2-continued

| | | | | | | | |
|---|---|---|---|---|---|---|---|
| Escherichia coli SKF 12140 | 47 | 16 | >128 | >128 | >128 | >128 | >128 |
| Pseudomonas aeruginosa ATCC 10145 | 4 | 128 | >128 | >128 | 128 | >128 | >128 |
| Proteus vulgaris X19H ATCC 881 | 79 | 128 | >128 | >128 | 128 | >128 | >128 |
| Candida albicans SKF 2270 | 145 | 64 | >128 | 2 | 64 | 2 | >128 |
| Tricophyton mentagrophytes | 634 | 128 | >128 | ≦0.13 | 128 | ≦0.13 | 128 |

| Strain | Int. code | MIC of the compounds of examples (μg/ml) | | | | | | |
|---|---|---|---|---|---|---|---|---|
| | | 18 | 19 | 21 | 23 | 25 | 30 | 32 |
| Staphilococcus aureus tour | 165 | 0.13 | 1 | 0.06 | 0.016 | 0.03 | 0.016 | 0.016 |
| Staphilococcus aureus tour ($10^6$ cfu/ml) | 165 | 0.13 | 1 | 0.13 | 0.03 | 0.06 | n.t. | 0.03 |
| Staph. aureus tour + 30% bovine serum | 165 | 2 | 8 | 1 | 2 | 1 | 1 | 0.25 |
| Staphilococcus epidermidis ATCC 12228 | 147 | 0.06 | 1 | 0.06 | 0.016 | 0.03 | 0.016 | 0.016 |
| Staphilococcus haemolyticus (clin. isolate) | 602 | 0.06 | 1 | 0.13 | 0.016 | 0.06 | 0.016 | 0.016 |
| Streptococcus pyogenes C 203 | 49 | 0.13 | 2 | 0.03 | 0.13 | 0.03 | 0.03 | 0.03 |
| Streptococcus pneumonieae UC 41 | 44 | 0.06 | 1 | 0.016 | 0.06 | 0.016 | 0.016 | 0.016 |
| Enterococcus faecalis ATCC 7080 | 149 | 0.13 | 2 | 0.06 | 0.03 | 0.06 | 0.03 | 0.03 |
| Clostridium perfringens ISS 30543 | 290 | 0.25 | 0.5 | n.t. | 0.03 | n.t. | n.t. | 0.016 |
| Bacteroides fragilis ATCC 9689 | 1010 | 0.5 | >128 | 0.13 | 0.06 | 0.06 | 0.06 | 0.06 |
| Propionibacterium acnes ATCC 6919 | 1014 | 0.016 | 0.5 | 0.004 | 0.008 | 0.008 | 0.016 | 0.004 |
| Neisseria gonorrhoeae ISM 68/126 | 997 | 0.13 | 64 | 0.03 | 0.06 | 0.03 | 0.03 | 0.06 |
| Haemophilus influenzae type b ATCC 19418 | 970 | 1 | 32 | 0.06 | 0.06 | 0.06 | 0.25 | 0.13 |
| Escherichia coli SKF 12140 | 47 | >128 | >128 | ≧128 | >128 | >128 | >128 | >128 |
| Pseudomonas aeruginosa ATCC 10145 | 4 | >128 | >128 | ≧128 | >128 | >128 | >128 | >128 |
| Proteus vulgaris X19H ATCC 881 | 79 | >128 | >128 | ≧128 | >128 | >128 | >128 | >128 |
| Candida albicans SKF 2270 | 145 | >128 | >128 | ≧128 | 8 | 32 | 16 | 18 |
| Tricophyton mentagrophytes | 634 | >128 | >128 | ≧128 | >128 | 32 | 16 | >128 | n.t. = not tested

The activity of some antibiotic derivatives of the invention against Gardnerella vaginalis and Trichomonas vaginalis is showed in table 3.

MIC for Gardnerella vaginalis was determined by an agar dilution method in Casman medium (Difco) supplemented with 5% (v/v) whole rabbit blood and 0.15% (v/v) lysed rabbit blood. Inocula were approximately $10^4$ cfu. Incubation was for 48 hours at 37° C. in nitrogen-carbon dioxide-hydrogen (80:10:10). MIC for Trichomonas vaginalis was determined by a broth dilution method in 0.2 ml of Trichomonas Culture Medium Base (Merck)+10% horse serum in flat-bottomed microtiter wells. The inoculum was approximately $10^5$ cells/ml. After 48 hours of incubation at 37° C. in nitrogen-carbon dioxide-hydrogen (80:10:10) the wells were viewed directly with a microscope to detect the presence of viable (motile) protozoa.

TABLE 3

| STRAIN | Int. code | MIC of the compounds of Examples | | | |
|---|---|---|---|---|---|
| | | 10 | 14 | 25 | 32 |
| Trichomonas vaginalis (clin. isol.) | TVL | 8 | 1 | n.t. | 2 |
| Gardnerella vaginalis ATCC 14018 | 332 | 2 | 1 | 0.06 | 0.13 | n.t. = not tested

The four antibiotic derivatives reported in table 3 were also tested on 11 clinical isolate of Gardnerella vaginalis; the MICs of all the compounds for these strains were similar to those determined for the ATCC strain 14018.

The above findings make the compound of the invention suitable for the treatment of vaginal infections.

According to the most recent views of the chemotherapy of vaginal infections, the patients in need of said treatment may be both the female affected by the infection and, in the case of chronic recurrent infections, also her male sexual partner. The compounds of the invention can be employed in pharmaceutical dosage forms particularly useful for the topical administration in the treatment of vaginal infections.

Topical dosage forms are provided including vaginal tablets, pessaries, creams, ointments, gels, suppositories, lotions, foams, powders, suspensions, drug delivery systems and the like which permit delivery and release of the active substance into the infection sites.

The pharmaceutical dosage forms contain the amino naphthazarin N-substituted of the invention and one or more excipients such as for example: starch, lactose, glucose, talc, cellulose for solid dosage forms; methocel, modified vegetable oils, mineral oils, polyalkylene glycols, fatty acids and alcohols and the like for semi-solid dosage forms; water, alkanols, glycerol, lanolin, polyethylene glycols, mineral oil, pharmaceutically acceptable organic solvents (e.g. DMSO, methyl-decyl-sulfoxide) and the like for liquid or semi-liquid dosage forms. The dosage forms may optionally contain other active ingredients or ingredients which preserve and favor the antimicrobial action of purpuromycin in the infection sites (e.g. antiseptics, emulsifiers, surfactants and the like).

Useful indications for the preparations of suitable topical dosage forms can be found in: Remington's Pharmaceutical Sciences, 17th Edition, 1985, 1985 (Merck Publishing Company, Easton, Pa.). The compounds of the invention can be employed in a micronized or ultramicronized form. The size of typical micronized and ultramicronized particles for use in the manufacture of pharmacological dosage forms of the invention is, for at least 85% of their total weight, of less than 10 and 5 micron diameter respectively.

The micronization may be carried out using different machinery based on various principles, as known by the person skilled in the art.

A preferred method is to micronize the compound, as such or mixed with appropriate excipients, using a fluid-energy mill. According to this system, the compound to be micronized is propelled by a violent gas stream into a circuit. Collisions of the compound particles against the walls of the circuit, as well as collisions of the particles with each other, lead to the pulverization of the particles. This machine can also be equipped with a recycling device that carries the larger, insufficiently pulverized particles, back into the grinding chamber. The major advantage of the fluid-energy mill lies in the fact that the build-up of the temperature in the micronization chamber is very low and the powder thus obtained is very homogeneous in particle-size, i.e. the range of particle-sizes is very narrow.

The particle-size of the product may be measured with the HIAC system, according to which the particle-size determination is based on the shadow caused by a particle hit by a light beam. The instrument essentially consists of a sensor which is formed by a light source and a photodetector on either side of the counting cell. A suspension of the test powder in water passes through this cell, the dimensions of which vary depending on the size range to be measured. Each particle, individually, interrupts some portion of a light beam generating a signal which is proportional to the area of the shadow of the particle.

This electric signal, suitably correlated to the diameter of a spherical standard particle which gives the same light absorption, yields the number of particles having a preselected diameter. The instrument may subdivide the measurement range (1-300 micron) in intervals of arbitrarily present dimensions. By this process it is possible to calculate the number of particles of each measurement range and correlate this number with the total number of particles contained in the sample.

The amount of active substance in the finished dosage forms depends on the minimal inhibitory concentration of active substance against the infection causative agents and its particular type of formulation. The dosage may obviously be adjusted according to the severity of the infection and the type of patients. Experimental tests for determining the sensitivity of the microorganisms isolated from the patient may also offer useful indication to select the appropriate dosage.

In general terms, the effective dosage ranges between 10 mg and 600 mg, preferably 100 mg and 400 mg, for each vaginal application once to three times daily. The course of treatment may last from 3 to 10 days or longer, if required.

Liquid or semi-liquid dosage forms such as, creams, lotions, ointments, foams and suspensions generally contain from 0.05 to 5 percent by weight of active compound. If necessary, this range may be broadened without any substantial modification of the characteristics of the respective dosage form.

Solid intravaginal unit dosage forms such as vaginal tablets and suppositories can be manufactured in different dosages. For instance, they may contain from 10 to 600 mg of active compound.

Preferred dosages are comprised between 100 and 400 mg.

Typical drug delivery systems incorporating 7'-amino naphthazarines N-substituted are formulated, for instance, with biodegradable polymers for controlled release such as those described at pages 106-119 of the book: Drug Delivery Systems. Fundamentals and Techniques—Edited by P. Johnson and J. G. Loyd-jones, 1987, Ellis Horwood Ltd. Chichester, England.

The following illustrative examples show some pharmaceutical dosage forms of 7'-methylamino purpuromycin for topical treatment of infectious vaginitis. The manufacture of the dosage forms is carried out according to commonly known procedures.

EXAMPLE 33

Vaginal Suppositories (hydrophilic)

| | |
|---|---|
| 7'-Methylaminopurpuromycin (micronized) | g 0.30 |
| Methyl-decyl-sulfoxide | g 0.30 |
| Carbowax 4000 | g 1.70 |
| Carbowax 1540 | g 0.80 |
| PEG 1000 monostearate | g 1.30 |

EXAMPLE 34

Vaginal Tablets

| | |
|---|---|
| 7'-Methylaminopurpuromycin (micronized) | g 0.300 |
| Lactose | g 0.096 |
| Sodium benzoate | g 0.030 |
| PVP K 30 | g 0.050 |
| Sodium bicarbonate | g 0.134 |
| Sodium citrate, acid | g 0.350 |

EXAMPLE 35

Anhydrous Cream

| | |
|---|---|
| 7'-Methylaminopurpuromycin (micronized) | g 2.00 |
| Methyl-decyl-sulfoxide | g 2.00 |
| Carbowax 6000 | g 25.00 |
| Stearyl alcohol | g 10.00 |
| Propylene glycol | g 61.00 |

EXAMPLE 36

Cream (o/w)

| | |
|---|---|
| 7'-Methylaminopurpuromycin (micronized) | g 2.00 |
| White petrolatum | g 12.00 |
| Liquid paraffin | g 12.00 |
| Cetyl alcohol | g 8.00 |
| Stearyl alcohol | g 3.50 |
| Sorbitan monolaurate | g 3.10 |
| Polyoxyethylene sorbitan monolaurate | g 3.00 |
| Methyl-decyl-sulfoxide | g 2.00 |
| Water | q.s. to g 100 |

EXAMPLE 37

Gel

| | |
|---|---|
| 7'-Methylaminopurpuromycin (micronized) | g 2.00 |
| Methyl-decyl-sulfoxide | g 2.00 |
| Propylene glycol | g 8.00 |
| Carbopol 934 | g 2.00 |
| Water | q.s. to g 100 |

The following are examples of synthesis of compounds of general formula I and are to be considered as illustrative and in no way limitative to the scope of the present invention.

Experimental conditions and parameters for all the examples were as follows:

Evaporation of solvents was carried out with a rotary evaporator at 45° C. under vacuum;

All compounds were purified by column chromatography using Silica 60 (0.06–0.2 mm, Merck) as stationary phase. The columns were previously washed with a 5% HCl solution and dried under vacuum up to a water content of about 7%, to partially deactivate the silica gel. Eluents were pressurized to 0.5 atm. with $N_2$;

For monitoring the reactions, chromatographic fractions, and purity of the compounds, HPLC analysis was applied, by using a Hewlett-Packard mod. 1090L instrument equipped with a UV detector at 254 nm and a Hibar LiChroCart column (125×4 mm) packed with LiChrosorb RP-18 (5 µm). Injection volume, 10 µl; flow rate, 1 ml/min; mobile phase: (A) $NaH_2PO_4$ 0.02M (pH 4.7); (B) $CH_3CN$; step gradients as follows:

| Method 1 | | | | | |
|---|---|---|---|---|---|
| Minutes | 0 | 2 | 20 | 25 | 30 |
| % B | 35 | 35 | 50 | 50 | 35 |
| Method 2 | | | | | |
| Minutes | 0 | 2 | 25 | 25 | |
| % B | 40 | 40 | 60 | 40 | |

All compounds were analyzed for C, H, N, using samples previously dried at 140° C. under $N_2$ atmosphere. Weight loss was determined by TGA at 140° C. and inorganic residue was determined after heating the samples at 900° C. in $O_2$ atmosphere. The analytical results were ±0.3% the theoretical values.

$^1$H-NMR spectra were obtained with a Bruker instrument AM 500 equipped with an Aspect 3000 console, at 500 MHz. The spectra were recorded at 40° C. in DMSO-$d_6$ solution, using tetramethylsilane (TMS, 0.00 ppm) as internal reference. NMR data are reported in table 1.

EXAMPLE 1

Compound A1 (Step a of scheme 1)

4-tetrahydropyranylpurpuromycin

To a solution of purpuromycin (4.35 g, 8.1 mmol) in 2000 ml of anhydrous $CH_2Cl_2$, 3,4-dihydro-2H-pyran (2.3 ml, 25.2 mmol) and anhydrous camphosulforic acid (1 mg) were added. The reaction mixture, maintained under $N_2$, was stirred under reflux for one hour. The solution was cooled to 5° C., added with 0.5 ml of pyridine and treated with 200 ml of water in a separatory funnel. The organic layer was separated and washed again with fresh water afterward dried on $MgSO_4$ and the solvent evaporated under vacuum. The bright red solid was treated with ethyl ether, recovered by under vacuum filtration and dried; yielding 4.3 g (82.2%). HPLC assay 96.40% $R_f$ 23.63 (method 1).

EXAMPLE 2

Compound B1 (Step b of scheme 1)

4-tetrahydropyranyl-4',9',10-O-triacetyl purpuromycin

To a suspension of 4-tetrahydropyranyl purpuromycin—prepared as in Example 1—(2 g, 3.2 mmol) in 50 ml of acetic anhydride, 3 ml of pyridine (distilled on $CaH_2$) was added and the resulting dark-red solution stirred at room temperature overnight. The yellow mixture was poured into 300 ml of ice/water and extracted with 600 ml of ethylacetate. The organic layer was washed with water (4 times), with 5% $NaHCO_3$ solution and again with water, then dried on $Na_2SO_4$ and evaporated under vacuum. The solid was treated with ethylether, filtered and dried under vacuum; yield 2.1 g (77%). A sample was recrystallized from ethylacetate/ethylether obtaining a yellow solid. HPLC $R_f$ 19.3 (method 1), 14.0 (method 2).

EXAMPLE 3

Compound C1 (Step c of scheme 1)

6'-Br-4-tetrahydropyranyl-4',9',10-O-triacetyl purpuromycin

To a solution of 4-tetrahydropyranyl-4',9',10-O-triacetyl purpuromycin—prepared as in Example 2—(3.96 g, 5 mmol) and pyridine (1.5 ml) in 500 ml of $CH_2Cl_2$, pyridine bromide perbromide (5 g, 14 mmol) was added and the mixture was stirred at room temperature overnight. The reaction mixture was washed with a solution of sodium metabisulfite then twice with water; the organic layer was dried on sodium sulfate and evaporated under vacuum. The solid was treated with a mixture ethylether/ethylacetate 9/1 then filtered, washed with ether and dried under vacuum; yield 3.2 g (92%). The crude material has been purified by column chromatography on $SiO_2$ eluting with $CH_2Cl_2$/ethylacetate. Fractions containing the pure product were pooled and evaporated and residue was treated with ethyl acetate, filtered, washed with ethyl ether and dried under vacuum. HPLC $R_f$ 21.7 (method 2).

EXAMPLE 4

Compound D1 (Step d of scheme 1)

6'-Br-4',9',10-O-triacetil-purpuromycin

To a solution of 6'-Br-4-tetrahydropyranyl-4',9',10-O-triacetyl purpuromycin—prepared as in Example 3—(10 g, 12 mmol) in of MeOH (1 l), 100 mg of p-toluensulfonic acid was added and the mixture stirred for 4 hours at 55° C. The solvent was evaporated and the yellow-orange residue, treated with ethyl ether, was filtered and dried under vacuum. The powder is a mixture of compound C1 and of a corresponding di-O-acetyl derivative (90%-10% respectively); Yield 8.3 g. HPLC $R_f$ 12.3 min (method 2).

EXAMPLE 5

Compound E1 (Step e of scheme 1)

6'-Br-7'-(2-dimethylaminoethylen)-amino purpuromycin 600 mg (0.81 mmol) of 6'-Br-4',9',10-O-triacetil-purpuromycin—prepared as in Example 4—were dissolved under $N_2$ in 150 ml of THF and then 2-(dimethylamino)ethylamine (356 µl, 3.2 mmol) was added; the mixture was stirred for 2 hours at room temperature. Acetic acid (220 µl) was added to the mixture and the solvent was evaporated under vacuum. The residue, treated with EtOH at 50° C., was filtered, washed with ethyl ether and dried under vacuum. A red-violet powder was obtained. Yield 550 mg; HPLC $R_f$ 7.47 min (method 1).

EXAMPLE 6

Compound G1 (Step f of scheme 1)

7'-(2-dimethylaminoethylen)amino purpuromycin hydrochloride

To a solution of 6'-Br-7'-(2-dimethylamino-ethylen)amino purpuromycin—prepared as in Example 5—(100 mg, 0.148 mmol) in MeOH (10 ml) and THF (30 ml), 80 mg of 5% Pd/C were added. This mixture was hydrogenated at room pressure and temperature for 2 hours. Few drops of N HCl were added to the mixture, till the colour turned from purple to red, and the catalyst was removed by filtration on Celite (filter aid). The solution was evaporated under vacuum and the residue was treated with EtOH, filtered, washed with ethyl ether and dried under vacuum. Yield 80 mg; HPLC $R_f$ 5.15 min (method 1).

EXAMPLE 7

Compound E2 (Step e of scheme 1)

6'-Br-7'-(phenylmethylen)amino purpuromycin

To a solution of 6'-Br-4',9',10-O-triacetil-purpuromycin—prepared as in Example 4—(300 mg, 0.433 mmol) in THF (100 ml), benzylamine (300 µl, 2.75 mmol) was added under stirring at room temperature. The reaction was over in 1.5 h. 300 µl of acetic acid were added and the solvent was evaporated under vacuum. The residue was treated with 10 ml of EtOH, filtered, washed with ethyl ether and dried under vacuum. Yield 300 mg; HPLC $R_f$ 26.88 min (method 1).

EXAMPLE 8

Compound F2 (Step f of scheme 1)

7'-(phenylmethylen)amino purpuromycin

A solution of 6'-Br-7'-(phenylmethylen)amino purpuromycin—prepared as in Example 7—(200 mg, 0.289 mmol) and CH3COONa (5 mg) in THF (60 ml) and MeOH (20 ml) was added to 25 mg of 5% Pd/C. The mixture was hydrogenated at atmospheric pressure and room temperature for 40 minutes. The catalyst was removed by filtration on Celite (filter aid) and the solvent was evaporated under vacuum. The crude solid was purified on silica gel flash column chromatography (50 g, 230–400 mesh; Merck) eluting with $CHCl_3$, $CHCl_3$—MeOH 95:5 and then $CHCl_3$—MeOH—$CF_3COOH$ 95:5:0.1%. Fractions containing the pure product were pooled and evaporated and the dark-red residue was treated with ethyl acetate, filtered, washed with ethyl ether and dried under vacuum. Yield 100 mg. HPLC $R_f$ 20.32 min (method 1).

EXAMPLE 9

Compound E3 (Step e of scheme 1)

6'-Br-7'-ethylamino purpuromycin

To a solution of 6'-Br-4',9',10-O-triacetil purpuromycin (500 mg, 0.81 mmol) in THF (150 ml) under $N_2$, 100 µl of 70% ethylamine in EtOH were added. The reaction was stirred at room-temperature for 20 hours, then few drops of N HCl were added till solution's colour changed from violet to red and the solvent was evaporated. The residue was treated with EtOH, filtered and washed with ethyl ether. Yield 430 mg of dried compound. HPLC $R_f$ 19.56 min (method 1).

EXAMPLE 10

Compound F3 (Step f of scheme 1)

7'-ethylamino purpuromycin

A solution of 6'-Br-7'-ethylamino purpuromycin—prepared as in Example 9—(390 mg, 0.618 mmol) and CH3COONa (30 mg) in THF (80 ml) and MeOH (20 ml) was added to 200 mg of 5% Pd/C. The mixture was hydrogenated at atmospheric pressure and room temperature for 4 hours and the product was then purified according to the procedure described in example 8. Yield 115 mg. HPLC $R_f$ 12.35 min (method 1).

EXAMPLE 11

Compound E4 (Step e of scheme 1)

6'-Br-7'-propylamino purpuromycin

To a solution of 6'-Br-4',9',10-O-triacetil-purpuromycin—prepared as in Example 4—(250 mg, 0.40 mmol) in THF (100 ml) propylamine (50 µl, 0.60 mmol) was added under $N_2$; the reaction mixture was stirred at room temperature for 20 hours. Acetic acid (50 µl) was added and the solvent evaporated. The residue was treated with EtOH, filtered, washed with ethyl ether and dried under vacuum. Yield 250 mg. HPLC $R_f$ 23.68 min (method 1).

EXAMPLE 12

Compound F4 (Step f of scheme 1)

7'-propylamino purpuromycin

A solution of 6'-Br-7'-propylamino purpuromycin—prepared as in Example 11—(200 mg, 0.311 mmol) and CH3COONa (30 mg) in THF (40 ml) and MeOH (10 ml) was added to 150 mg of 5% Pd/C. The mixture was hydrogenated at atmospheric pressure and room temperature for 2 hours. The final product was purified according to the procedure of example 8. Yield 85 mg. HPLC $R_f$ 16.38 mm (method 1).

EXAMPLE 13

Compound E5 (Step e of scheme 1)

6'-Br-7'-methylamino purpuromycin

To a solution of 6'-Br-4',9',10-O-triacetil-purpuromycin—prepared as in Example 4—(2.42 g, 3.2 mmol) in THF (500 ml), a 35% solution of $CH_3NH_2$ in water (4.62 ml, 4.88 mmol) was added under stirring at 20° C. and under $N_2$. After 50 minutes the reaction was stopped adding 60 ml of N HCl. The solvent was evaporated under vacuum and the wet residue was diluted with water and centrifuged. The red compound was dissolved in acetone and the solution dried over NaSO4, then 20 g of silica-gel was added and the solvent evaporated. The residue was loaded on the top of a chromatographic column containing 150 mg of silica-gel. The column was eluted with $CH_2Cl_2$ (5 l). Fractions (50 ml) containing compound E5 with purity >90% (HPLC assay) were pooled, the solvent was evaporated and the residue treated with ethyl ether was filtered and dried. Yield 420 mg; HPLC $R_f$ 15.46 min (method 1), $R_f$ 12.00 min (method 2).

EXAMPLE 14

Compound F5 (Step f of scheme 1)

7'-methylamino purpuromycin

A solution of 6'-Br-7'-methylamino purpuromycin—prepared as in Example 13—(400 mg, 0.65 mmol) and CH$_3$COONa (32 mg) in THF (90 mL) and MeOH (20 mL) was added to 215 mg of 5% Pd/C. The mixture was hydrogenated at room temperature and atmospheric pressure. The reaction was worked up in 1.5 hours, the mixture was acidified with N HCl (250 µl), the catalyst filtered on Celite and the solvent evaporated. The crude material was purified by column chromatography on 40 g of silica-gel eluting with CHCl$_3$ for removing impurities then eluting compound F5 with CHCl$_3$:MeOH (99:1). Fractions were collected, the solvent evaporated and the dark-red solid treated with ethyl ether, filtered and dried. Yield 110 mg; HPLC $R_f$ 9.25 mm (method 1).

EXAMPLE 15

Compound E6 (Step e of scheme 1)

6'-Br-7'-(cyanomethylen)amino purpuromycin

To a solution of 6'-Br-4',9',10-O-triacetil-purpuromycin—prepared as in Example 4—(613 mg, 0.81 mmol) in dimethylformamide (100 mL), cyanomethylamine hydrocloride (374.7 mg, 4.05 mmol) and triethylamine (450,8 µl, 3.24 mmol) were added. The reaction mixture was stirred at room temperature for 20 hours. The solution was acidified to pH 3 by adding few drops of N HCl and then diluted with water till complete precipitation of a red compound. The suspension was centrifuged, the liquid discharged and the solid dissolved in acetone. After evaporation of the solvent under vacuum, the residue was treated with ethyl ether, filtered and dried. Yield 500 mg. HPLC $R_f$ 12.27 min (method 1).

EXAMPLE 16

Compound F6 (Step f of scheme 1)

7'-(cyanomethylen)amino purpuromycin

A solution of 6'-Br-7'-(cyanomethylen)amino purpuromycin—prepared as in Example 15—(100 mg, 0.156 mmol) and CH$_3$COONa (7.5 mg) in THF (23 ml) and MeOH (6 ml) was added to 5% Pd/C (100 mg). The hydrogenation was carried out at room temperature and atmospheric pressure for 62 hours. The catalyst was removed by filtration under vacuum on Celite then the solvent was evaporated. The crude compound was purified by column chromatography on 15 g of silica gel, eluting with CHCl$_3$ containing increasing amount of MeOH from 0.5% to 20%. Fractions containing more than 92% (HPLC) of compound F6 were pooled and the product recovered by solvent evaporation. Yield 30 mg. HPLC $R_f$ 8.37 min (method 1).

EXAMPLE 17

Compound E7 (Step e of scheme 1)

6'-Br-7'-(2-(N-BOC-amino)ethylamino)purpuromycin

To a solution of 6'-Br-4',9',10-O-triacetil-purpuromycin—prepared as in Example 4—(61.3 mg, 0.081mmol) in dimethylformamide (DMF)(10 ml), N-Boc-ethylene-diamine (65 mg, 0.405 mmol) was added. The reaction mixture was stirred at room temperature for 2 hours. The solution was acidified to pH 3 with few drops of N HCl and water was added till complete precipitation of the product. The suspension was centrifuged, the red solid dissolved in CH$_2$Cl$_2$ and the organic layer washed with water. The red organic solution was separated, dried over CaCl$_2$ and evaporated. The residue treated with ethyl ether was filtered and dried. Yield 45 mg. HPLC $R_f$ 20.56 min (method 1).

EXAMPLE 18

Compound F7 (Step f of scheme 1)

7'-(2-(N-BOC-amino)ethylen)-amino purpuromycin

A solution of 6'-Br-7'-(2-(N-BOC-amino)ethylen)-amino purpuromycin—prepared as in Example 17—(100 mg, 0.134 mmol) and CH$_3$COONa (6.5 mg) in THF (23 ml) and MeOH (6 ml) was added to 5% Pd/C (100 mg). The reaction was carried out at room temperature and atmospheric pressure for 3.5 hours. The catalyst was removed by filtration on Celite under vacuum then the solvent was evaporated. The residue was dissolved in CH$_2$Cl$_2$—MeOH (99:1), the solution washed with acidic water and twice with distilled water; the organic layer was dried over NaSO$_4$ and evaporated. The residue was treated with ether, filtered and dried under vacuum. Yield 66 mg. HPLC $R_f$ 16.14 min (method 1).

EXAMPLE 19

Compound G7

7'-(2-aminoethylen)-amino purpuromycin trifluoroacetate

To a solution of 7'-(2-(N-BOC-amino)ethylen)-amino purpuromycin—prepared as in Example 18—(175 mg) in CH$_2$Cl$_2$ (35 ml), CF$_3$COOH (1.75 ml) was added under stirring; the solution was maintained at room temperature for 3 hours. The solvent was evaporated and the residue, treated with ether, was filtered and dried under vacuum. Yield 178 mg. HPLC $R_f$ 4.15 min (method 1).

EXAMPLE 20

Compound E8 (Step e of scheme 1)

6'-Br-7'-(2-hydroxyethylen)-amino purpuromycin

To a solution of 6'-Br-4',9',10-O-triacetil-purpuromycin—prepared as in Example 4—(500 mg 0.672 mmol) in DMF (100 ml), ethanolamine (173 µl, 2.88 mmol) was added and the mixture was stirred at room temperature for 6 hours. Drops of N HCl were added till colour change from violet to red, water was added and the suspension centrifuged. The compound was dissolved in acetone which was then evaporated under vacuum; toluene was added in the flask and evaporation was continued to dryness. The residue was dissolved in ether, filtered and dried under vacuum. Yield 425 mg. HPLC $R_f$ 8.77 min (method 1).

EXAMPLE 21

Compound F8 (Step f of scheme 1)

7'-(2-hydroxyethylen)-amino purpuromycin

A solution of 6'-Br-7'-(2-hydroxyethylamino) purpuromycin—prepared as in Example 20—(350 mg, 0.54 mmol) and CH$_3$COONa (30 mg) in THF (80 mL) and MeOH (20 mL) was added to 5% Pd/C (200 mg); the mixture was hydrogenated at room temperature and atmospheric pressure for 4 hours. The catalyst was removed by filtration on Celite and the solvent evaporated. The residue was dissolved in a mixture of acetone-methanol-methylenechloride (30:10:60); to this solution 3.5 g of silica gel were added and the solvent evaporated. The powder was loaded on the top of a chromatographic column containing 70 g of silica gel and the compound F8 was eluted with CH$_2$Cl$_2$—MeOH 99:1. Fractions containing the pure compound were pooled and the solvent evaporated to dryness. Yield 78 mg. HPLC R$_f$ 4.80 min (method 1).

EXAMPLE 22

Compound E9 (Step e of scheme 1)

6'-Br-7'-(2,2,2-trifluoroethylen)-amino purpuromycin

A solution of 6'-Br-4',9',10-O-triacetil-purpuromycin—prepared as in Example 4—(500 mg, 0.672 mmol) and CF$_3$CH$_2$NH$_2$ (800 µl, 10 mmol) in DMF (50 ml) was stirred at room temperature for 3 days. The reaction was added with 50 µl of N HCl, then diluted with water and centrifuged. The solid, dissolved in CH$_2$Cl$_2$, was loaded on the top of a chromatographic column containing 50 g of silica gel and the compound E9 was eluted with CH$_2$Cl$_2$. Fractions containing the pure compound were pooled and the solvent evaporated to dryness. Yield 178 mg. HPLC R$_f$ 20.48 min (method 1).

EXAMPLE 23

Compound F9 (Step f of scheme 1)

7'-(2,2,2-trifluoroethylen)-amino purpuromycin

A solution of 6'-Br-7'-(2,2,2-trifluoroethylen)-amino purpuromycin—prepared as in Example 22—(863 mg, 1.26 mmol) and CH$_3$COONa (105 mg) in THF (200 ml) and MeOH (50 ml) was added to 5% Pd/C (200 mg). The reaction was carried out at room temperature and atmospheric pressure for 1 hour. The catalyst was removed by filtration on Celite and the solvent evaporated. The residue was dissolved in acetone-methanol-methylenechloride (30:10:60); to this solution 3.5 g of silica gel were added and the solvent evaporated. The powder was loaded on the top of a chromatographic column containing 30 g of silica gel and F9 was eluted with CH$_2$Cl$_2$—MeOH 99:1. Fractions containing the pure compound were pooled and the solvent evaporated to dryness. Yield 60 mg. HPLC R$_f$ 16.31 min (method 1).

EXAMPLE 24

Compound E10 (Steps e and d of scheme 1)

7'-amino-6'-bromo purpuromycin

To a solution of 6'-Br-4',9',10-O-triacetil-purpuromycin of the Example 4 (3.2 g, 3.8 mmol) in 350 ml of THF 3.5 ml of NH$_4$OH was added (concentration about 25% w/v). The yellow-brown solution become violet and was stirred at room temperature for 18 hours. After this time the starting material was not longer detectable by HPLC while were present two major peaks, one less lipophilic (27%), the second more lipophilic (68%) than 4-tetra-hydropyranyl-4',9',10-O-triacetyl purpuromycin (R$_f$ 18.7 and 22.5 min respectively). The two compounds have been identified as 6'-bromo- 4-tetrahydropyranyl purpuromycin and 7'-amino-6'-bromo- 4-tetrahydropyranyl purpuromycin.

The solvent of the final violet suspension was evaporated under vacuum and the residue was dissolved in acetone (200 ml); into this solution under stirring was added 1N HCl (12 ml) and the mixture heated to 35°–40° C. for two hours. The mixture was evaporated and the residue purified by column chromatography on SiO$_2$ eluting with a gradient of MeOH (1 to 10%) in a solution of CHCl$_3$ containing 0.1% of CH$_3$COOH. From this chromatography the title compound (HPLC R$_f$ 6.0 method 1) and 6'-Br purpuromycin (which treated again with NH$_4$OH gives the title compound) were obtained.

EXAMPLE 25

Compound F10 (Step f of scheme 1)

7'-Aminopurpuromycin

To a solution of 7'-amino-6'-bromopurpuromycin of Example 24 above, (500 mg, 0.8 mmol) in 50 ml of THF, under N$_2$, MeOH (30 ml), anhydrous sodium acetate (100 mg) and 5% Pd/C (20 mg) were added. The mixture was hydrogenated at 1 atm. and room temperature for 1.5 hour. The catalyst was filtered on Celite (filter aid) and the solvent evaporated; the residue suspended in water and acidified with 1N HCl was extracted with chloroform. The organic layer was washed with water, dried on sodium sulfate and evaporated; the solid treated with ethylether was filtered and dried under vacuum; yielding 350 mg, HPLC R$_f$ 7.4, method 1.

EXAMPLE 26

4-Chloropurpuromycin (starting material for producing γ-rubromicin amino-derivatives)

Purpuromycin (200 mg, 0.37 mmol) was stirred with 10 ml of SOCl$_2$ and 10 ml of pyridine at room temperature under nitrogen for 2 hours. The solvent was then evaporated by bubbling into the mixture a cold NaOH solution.

The residue was stripped two times with toluene then dissolved into 5 ml of CHCl$_3$ and loaded on the top of a chromatographic column containing 20 g of Silica Gel. The product was eluted as a mixture of 4-Cl-enantiomers (28% peak A, 72% peak B) with CHCl$_3$. Fractions were pooled and evaporated yielding 110 mg; HPLC R$_f$ 14.7 (A) and 18.9 (B) min (method 1).

EXAMPLE 27

4-Chloro-4',9',10-O-triacetylpurpuromycin

By substantially following the procedure described in Example 2 but starting from 4-Chloropurpuromycin of Example 26 the title compound was obtained. The crude material was purified on $SiO_2$ eluting with $CHCl_3$-ethylacetate 9:1, yield 50%. The two enantiomers shows HPLC, $R_f$ 12.2 and 15.8 min (method 1).

EXAMPLE 28

6'-bromo-4-chloro-4',9',10-O-triacetyl-purpuromycin

By substantially following the procedure described in Example 3 but starting from 10 g of 4-Chloro-4',9',10-triacetyl purpuromycin prepared according to Example 27 the title compound was obtained. The crude material was purified on $SiO_2$ eluting with $CHCl_3$ ethyl acetate, 9:1, yield 40%. HPLC $R_f$ 19.0 and 21.3 min (method 1).

EXAMPLE 29

7'-amino-6'-bromo-4-Chloro purpuromycin

By substantially following the procedure described in Example 24 but starting from 700 mg of 6'-bromo-4-chloro-4',9',10-O-triacetylpurpuromycin of Example 28 the title compound was obtained. Purification on HPLC preparative Waters mod. 590 column RP- 18 Lichrosorb (1Kg), flow: 40 ml/min, eluent 65% $CH_3CN$-35% $H_2O$ pH=4 ($CH_3COOH$); yield 250 mg, HPLC $R_f$ 16.8 and 21.3 min (method 1).

EXAMPLE 30

Compound F11

7'-Amino-γ-rubromycin

By substantially following the procedure described in Example 25 but using 200 mg of 7'-amino-6'-bromo-4-chloro purpuromycin as starting material, the title compound was obtained. The hydrogenation was carried out with 5% Pd/C in THF/MeOH adding $CH_3COONa$. The reaction was considered completed after 90 minutes. Total yield (without purification) 90% HPLC: $R_f$ 11.6 min (method 2).

EXAMPLE 31

Compound E5'

6'-Br-4-Cl-7'-methylamino purpuromycin (enantiomeric mixture)

500 mg (0.08 mmol) of 6'-Br-7'-methylamino purpuromycin—prepared as in Example 13—were added under stirring to 10 ml of thionyl chloride cooled at 0° C. After 10 minutes the suspension was allowed to reach room temperature while keeping the stirring for 2 hours. The solvent was removed under vacuum and the residue, dissolved in $CH_2Cl_2$, was loaded on the top of a chromatographic column containing 50 g of silica gel and eluted with $CH_2Cl_2$. Fractions containing the two enantiomers were pooled and the solvent evaporated to dryness. Yield 300 mg. HPLC $R_f$ 20.9 and 25.8 min (method 2).

EXAMPLE 32

Compound F12

7'-methylamino γ-rubromycin

A solution of 6'-Br-4-$C_1$-7'-methylamino purpuromycin prepared as in Example 31—(750 mg, 1.18 mmol) in THF (200 ml) containing triethylamine (3.15 μl, 2.36 mmol) and MeOH (50 ml) was added to 5% Pd/C (750 mg). The reaction was carried out at room temperature and atmospheric pressure for 1 hour. The catalyst was removed by filtration on Celite and the solvent evaporated. The residue was loaded on the top of a chromatographic column containing 70 g of silica gel and eluted with $CH_2Cl_2$. Fractions containing compound F10 with purity >80% (HPLC assay) were pooled and the solvent was evaporated. The residue was purified by preparative HPLC with a Beckman mod. 350 instrument equipped with a 254 nm UV detector and a chromatografic column packed with LiChrosorb RP-18 (7 μm). Flow rate, 21 ml/min; mobile phase: (A) $NaH_2PO_4$ 0.02M (pH 4.7); (B) $CH_3CN$; step gradient as follows:

Minutes 0 8 35 40 45

%B 50 52 65 70 50

Yield 150 mg; HPLC $R_f$ 15.8 min (method 2).

The following table 1 shows the $^1$HNMR shifts of the final products obtained in the above examples.

TABLE I $^1$HNMR Spectra
Recorded at 500 Mhz with tetramethylsilane as internal standard (TMS, = .00 ppm)

| Comp. of Example | $^1$H-NMR (DMSOd$_6$) δ (ppm) |
|---|---|
| 6 | 2.50, 2.77, 3-H(2H,m); 3.41, 3.54, 3'-H(2H, $J_{gem}$ 18); 4.94, 4-H(m); 5.77, 6'-H(s); 7.45, 5-H(s); 7.65, 6-H(s); 3.82, 7-$CO_2CH_3$(s); 2.80, 3.31, 3.57, 7'-N-alk-X; 7.45, 7'-NH; 5.83, 4-OH(s) |
| 8 | 2.50, 2.77, 3-H(2H, m); 3.39, 3.59, 3'-H(2H, $J_{gem}$ 18); 4.95, 4-H(m); 5.50, 6'-H(s); 7.50, 5-H(s); 7.74, 6-H(s); 3.87, 7-$CO_2CH_3$(s); 4.47, 7.25, 7.33, 7'-N-alk-X; 7.75, 7'-NH; |
| 10 | 2.49, 2.77, 3-H(2H, m); 3.40, 3.60, 3'-H(2H, $J_{gem}$ 18); 4.96, 4-H(m); 5.59, 6'-H(s); 7.50, 5-H(s); 7.74, 6-H(s); 3.87, 7-$CO_2CH_3$(s); 14.15, 4'-OH; 1.16, 3.20, 7'-N-alk-X; 7.79, 7'-NH; |
| 12 | 2.48, 2.76, 3-H(2H, m); 3.40, 3.60, 3'-H(2H, $J_{gem}$ 18); 4.96, 4-H(m); 5.70, 6'-H(s); 7.50, 5-H(s); 7.74, 6-H(s); 3.87, 7-$CO_2CH_3$(s); 14.13, 4'-OH(s); 11.55, 9'-OH(s); 10.61, 10-OH(s); 0.89, 1.60, 3.17, 7'-N-alk-X; 7.82, 7'-NH; |
| 14 | 2.50, 2.77, 3-H(2H, m); 3.41, 3.51, 3'-H(2H, $J_{gem}$ 18); 4.97, 4-H(m); 5.52, 6'-H(s); 7.51, 5-H(s); 7.76, 6-H(s); 3.88, 7-$CO_2CH_3$(s); 14.17, 4'-OH; 11.55, 9'-OH; 10.65, 10-OH; 2.83, 7'-N-alk-X; 7.92, 7'-NH; 5.83, 4-OH(m) |
| 16 | 2.50, 2.77, 3-H(2H, m); 3.43, 3.62, 3'-H(2H, $J_{gem}$ 18); 4.96, 4-H(m); 5.89, 6'-H(s); 7.50, 5-H(s); 7.73, 6-H(s); 3.87, 7-$CO_2CH_3$(s); 4.43, 7'-N-alk-X; 8.02, 7'-NH; 5.87, 4-OH(m) |
| 18 | 2.50, 2.80, 3-H(2H, m); 3.40, 3.62, 3'-H(2H, $J_{gem}$ 18); 4.96, 4-H(m); 5.69, 6'-H(s); 7.51, 5-H(s); 7.77, 6-H(s); 3.87, 7-$CO_2CH_3$(s); 14.15, 4'-OH; 11.55, 9'-OH; 10.67, 10-OH; 1.36, 3.14, 3.32, 7'-N-alk-X; 7.00, 7.20, 7'-NH; |

TABLE I-continued

$^1$HNMR Spectra
Recorded at 500 Mhz with tetramethylsilane as internal standard (TMS, = .00 ppm)

| Comp. of Example | $^1$H-NMR (DMSOd$_6$) δ (ppm) |
|---|---|
| 19 | 2.50, 2.80, 3-H(2H, m); 3.40, 3.62, 3'-H(2H, J$_{gem}$ 18); 4.96, 4-H(m); 5.79, 6'-H(s); 7.51, 5-H(s); 7.77, 6-H(s); 3.87, 7-CO$_2$CH$_3$(s); 3.01, 3.44, 7'-N-alk-X; 7.80, 7'-NH; |
| 21 | 2.50, 2.80, 3-H(2H, m); 3.41, 3.60, 3'-H(2H, J$_{gem}$ 18); 4.95, 4-H(m); 5.66, 6'-H(s); 7.50, 5-H(s); 7.75, 6-H(s); 3.87, 7-CO$_2$CH$_3$(s); 14.13, 4'-OH; 11.53, 9'-OH; 10.67, 10-OH; 1.36, 3.14, 3.32, 7'-N-alk-X; 7.00, 7.20, 7'-NH; |
| 23 | 2.50, 2.80, 3-H(2H, m); 3.41, 3.62, 3'-H(2H, J$_{gem}$ 18); 4.95, 4-H(m); 6.02, 6'-H(s); 7.50, 5-H(s); 7.75, 6-H(s); 3.87, 7-CO$_2$CH$_3$(s); 13.75, 4'-OH; 11.52, 9'-OH; 10.65, 10-OH; 4.14, 7'-N-alk-X; 7.92, 7'-NH; 7.96, 4-OH(m); |
| 25 | 2.49, 2.77, 3-H(2H,m); 3.39, 3.59, 3'-H(2H, J$_{gem}$ 18); 4.95, 4-H(m); 5.73, 6'-H(s); 7.50, 5-H(s); 7.75, 6-H(s); 3.88, 7 CO$_2$CH$_3$(s); 14.03, 4'-OH; 11.66, 9'-OH; 10.64, 10-OH(m) |
| 30 | 3.05, 3-H(2H, m); 3.44, 3.58, 3'-H(2H, J$_{gem}$ 18); 2.33, 4-H(m); 5.73, 6'-H(s); 7.28, 5-H(s); 7.68, 6-H(s); 3.87, 7-CO$_2$CH$_3$(s); 14.10, 4'-OH; 11.55, 9'-OH; 10.65, 10-OH |
| 32 | 3.01, 3.14, 3-H(2H, m); 3.45, 3.57, 3'-H(2H, J$_{gem}$ 18); 2.35, 2.55, 4-H(2H, m); 5.48, 6'-H(s); 7.21, 5-H(s); 7.62, 6-H(s); 3.87, 7-CO$_2$CH$_3$(s); 14.14, 4'-OH; 11.52, 9'-OH; 10.64, 10-OH; 2.81, 7'-N-alk-X; 7.86, 7'-NH. |

We claim:
1. Compound of general formula V

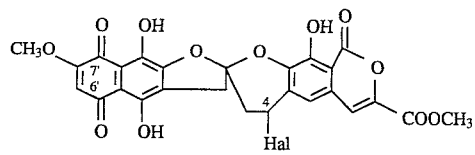

wherein Hal is a chlorine or bromine atom.

2. Process for preparing a compound of claim 1 by reacting purpuromycin with a chlorinating or brominating agent in order to insert in position 4 a chlorine or bromine atom.

3. Process according to claim 2 wherein the chlorinating or brominating agent is triphenyl phosphine (PhP$_3$) in CCl$_4$, polymer supported PhP$_3$ in CCl$_4$, PhP$_3$.Cl$_2$, PCl$_3$ and ZnCl$_2$ in dimethylformammide, AsCl$_3$, PBr$_3$, (CH$_3$)$_2$S.Br$_2$ or SOCl$_2$.

4. Process according to claim 2 wherein the chlorinating agent is SOCl$_2$ in the presence of pyridine.

* * * * *